(12) United States Patent
Kindiger

(10) Patent No.: US 11,154,022 B2
(45) Date of Patent: Oct. 26, 2021

(54) PRODUCTION OF HAPLOID LOLIUM

(71) Applicant: The United States of America, as represented by the Secretary of Agriculture, Washington, DC (US)

(72) Inventor: Bryan K. Kindiger, El Reno, OK (US)

(73) Assignee: The United States of America, as represented by the Secretary of Agriculture, Washington, DC (US)

( * ) Notice: Subject to any disclaimer, the term of this patent is extended or adjusted under 35 U.S.C. 154(b) by 94 days.

(21) Appl. No.: 16/201,262

(22) Filed: Nov. 27, 2018

(65) Prior Publication Data

US 2020/0163299 A1      May 28, 2020

(51) Int. Cl.
     *A01H 1/08*      (2006.01)
     *A01H 6/46*      (2018.01)
     *A01H 5/12*      (2018.01)

(52) U.S. Cl.
     CPC .................. *A01H 1/08* (2013.01); *A01H 5/12* (2013.01); *A01H 6/463* (2018.05)

(58) Field of Classification Search
     CPC ............. A01H 1/08; A01H 6/463; A01H 5/12
     See application file for complete search history.

(56) References Cited

U.S. PATENT DOCUMENTS

| 2013/0097724 A1 | 4/2013 | Kindiger |
| 2018/0014488 A1 | 1/2018 | Van Dun |

FOREIGN PATENT DOCUMENTS

| CN | 102224801 A | 10/2011 |
| CN | 103081797 A | 5/2013 |
| CN | 106171965 A | 8/2018 |

OTHER PUBLICATIONS

Kindiger (Jan. 2012, "Notification of the Release of Annual Ryegrass Genetic Stock IL1", Journal of Plant Registrations 6(1): 217-220).*
Kindiger (Jan. 2012, "Notification of the Release of Annual Ryegrass Genetic Stock IL1", Journal of Plant Registrations 6(1): 217-220). (Year: 2012).*
International Search Report for PCT/US2019/062566 dated Mar. 13, 2020.
Written Opinion for PCT/US2019/062566 dated Mar. 13, 2020.

* cited by examiner

*Primary Examiner* — Russell Kallis
(74) *Attorney, Agent, or Firm* — John Fado; Ariel Atkinson

(57) ABSTRACT

A method for producing haploid *Lolium* plants may start with providing a *Lolium multiflorum* inducer line, the *L. multiflorum* inducer line having the ability to induce mitotic genome instability and haploid sectoring when hybridized as a maternal parent with a *Lolium* sp. paternal parent, such as previously disclosed lines IL1 and IL2. The inducer line may then be crossed with a *Lolium* sp. to generate F1 plants, and the F1 plants may be self-fertilized so as to recover seed from the selfed plant. The recovered seed may then be planted to generate one or more F2 plants, and at least one of the F2 plants may be a haploid *Lolium* plant.

5 Claims, 2 Drawing Sheets

PRODUCTION OF HAPLOID LOLIUM

BACKGROUND

Haploid induction systems result in the generation of either maternal or paternal haploids that can efficiently advance genetic gains through gamete selection or a dihaploid production breeding or selection program. The standard approach for the production of haploids in *Lolium* sp. is almost exclusively limited to microspore or anther culture approaches (Palmer and Keller, Challenges and Limitations to the use of Haploidy in Crop Improvement, Biotechnology in Agriculture and Forestry, Vol. 56, pp. 295-303, 2005; Tuvesso et al. Molecular markers and doubled haploids in European plant breeding programmes, *Euphytica* 58:305-312, 2007; Dunwell, Haploids in flowering plants: Origins and exploitation, *Biotech. J.* 8:377-424, 2010). Haploidy, as generated through microspore or anther culture, is highly labor intensive, expensive and restricted by necessitating the plant being cultured to possess a genotype amendable to such methodology. Within the *Lolium* genus, microspore derived levels of haploid generation are known to range from 1-5%. Such haploids, when identified, are then subjected to a mitotic inhibitor in order to double the chromosome number to produce homozygous or dihaploid (DH) lines. These materials can then be utilized for advanced selection or breeding methodologies or molecular marker assisted breeding techniques (Martinez et al., On the use of double haploids for detecting QTL in outbred populations, *Heredity* 88:423-431, 2002; Chang and Coe, Doubled haploids, Biotechnology in Agriculture and Forestry. Vol. 63, pp. 127-142, 2009; Begheyn et al. *Review*: Haploid and Double Haploid Techniques in Perennial Ryegrass (*Lolium perenne* L.) to Advance Research and Breeding, Agron. 60:1-17, 2016). Several recent reviews regarding the generation and utilization of haploids and dihaploids in *Lolium* sp. have been published and significant details on the history, methods and outcomes of that prior research can be gleaned from those reviews (Chang and Coe, 2009; Geiger, Doubled haploids, Maize Handbook. Vol. II: Genetics and Genomics, pp. 641-659, 2009; Dunwell, 2010; and Begheyn et al., 2016).

In other instances, inducer lines (Fehr, Homozygous lines from double haploids, Principles of cultivar development. Vol. 1, pp: 337-358. 1984) can be utilized to produce haploids and eventually DH lines possessing only the maternal genotype that can then be eventually introduced into breeding programs (Forster and Thomas, Doubled haploids in genetics and plant breeding, Plant Breed Rev. 25:57-88, 2005). In addition, there are systems where paternal haploids are generated when the maternal or egg parent represents the inducer line, such as seen with the indeterminate gametophyte system of maize (Kermicle, Androgenesis Conditioned by a Mutation in Maize, *Science* 166:1422-1424, 1969; Rotarenco and Chalyk, Selection at the level of haploid sporophyte and its influence on the traits of diploid plants in maize, *Genetika* 32:479-485, 2000). Each of the above methods produces haploids through novel meiotic behaviors found in the respective lines.

Previously, an approach utilizing annual ryegrass (*Lolium perenne* L. subsp. *multiflorum* (Lam.) Husnot (syn. *Lolium multiflorum* Lam.) lines called IL1 and IL2 (Kindiger and Singh, Registration of Annual Ryegrass Genetic Stock IL2, *J. of Plant Reg.* 5:254-256, 2011; Kindiger, Notification of the Release of Annual Ryegrass Genetic Stock IL1, J. of Plant Reg. 6:117-120, 2012) has been described. IL1 and IL2 have the ability to induce mitotic genome instability and haploid sectoring when hybridized with tall fescue (*Lolium arundinaceum* (Schreb.) Darbysh.) (syn. *Festuca arundinacea* Schreb.) (Kindiger, Generation of Paternal Dihaploids in Tall fescue, Grassland Science. 62:243-247, 2016).

All of the references cited herein, including U.S. Patents and U.S. Patent Application Publications, are incorporated by reference in their entirety.

Mention of trade names or commercial products in this publication is solely for the purpose of providing specific information and does not imply recommendation or endorsement by the U.S. Department of Agriculture.

SUMMARY

This research describes the generation of haploid genotypes following the hybridization of *L. multiflorum* or *L. perenne* genotypes to an inducer line, herein also referred to as an IL line. The principal advantage to this haploid inducement approach is that microspore methods or other culture approaches are not utilized.

According to one embodiment of the invention, a method for producing haploid *Lolium* plants may include: (1) providing a *Lolium multiflorum* inducer line, the *L. multiflorum* inducer line having the ability to induce mitotic genome instability and haploid sectoring when hybridized as a maternal parent with a *Lolium* sp. paternal parent, (2) crossing the *L. multiflorum* inducer line with a *Lolium* sp. to generate F1 plants, (3) self-fertilizing at least one of the generated F1 plants, (4) recovering and planting seed from the at least one self-fertilized F1 plant to generate one or more F2 plants, and (5) growing said one or more F2 plants, and at least one of the one or more F2 plants is a haploid *Lolium* plant.

According to a further aspect of the invention, the *L. multiflorum* inducer line is one of: IL1 (ATCC deposit accession no. PTA-10229) and IL2 (ATCC deposit accession no. PTA-10315).

According to a further aspect of the invention, the *L. multiflorum* inducer line is used as the maternal parent.

Another embodiment of the invention may be the F2 haploid *Lolium* plant produced by the above method.

BRIEF DESCRIPTION OF THE FIGURES

Advantages of embodiments of the present invention will be apparent from the following detailed description of the exemplary embodiments. The following detailed description should be considered in conjunction with the accompanying FIGURES in which.

Exemplary

Exemplary

Figure 1A:
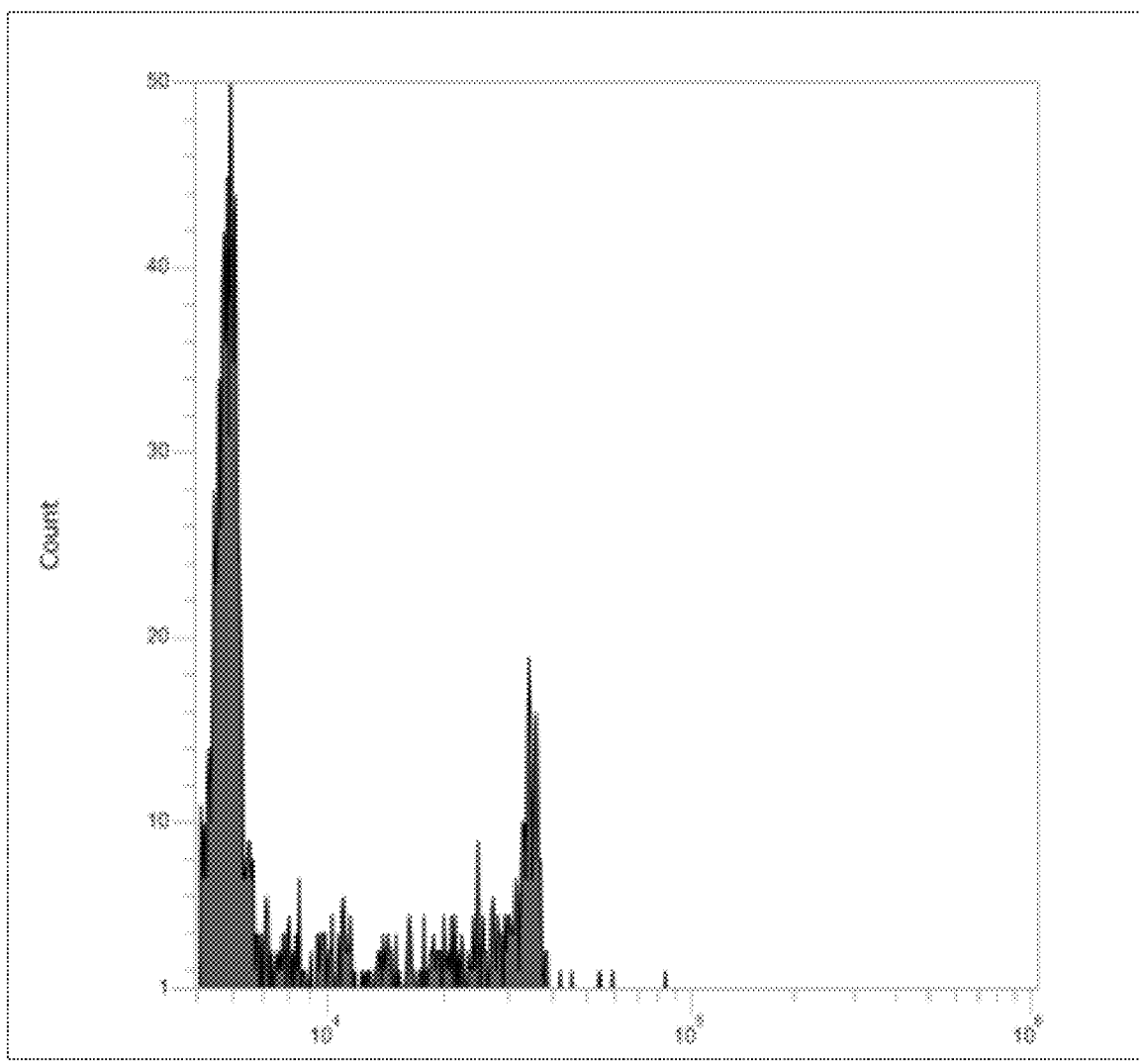
FIG. 1A shows a flow cytogram showing the presence of a large haploid sector in an F1 hybrid, as well as a small sector indicating a tetraploid recovery.

STATEMENT REGARDING DEPOSIT OF BIOLOGICAL MATERIAL UNDER THE TERMS OF THE BUDAPEST TREATY

A sample of at least 2,500 seeds of each of the *Lolium multiflorum* lines referred to herein as inducer line IL-1 and inducer line IL-2, were deposited under the conditions of the Budapest Treaty with the American Type Culture Collection (10801 University Blvd, Manassas, Va., 20110-2209, USA) on Jul. 22, 2009, and Aug. 28, 2009, respectively, and were assigned deposit accession nos. ATCC PTA-10229 and ATCC PTA-10315, respectively. The lines have no restrictions on their availability to the public.

DETAILED DESCRIPTION

Aspects of the invention are disclosed in the following description and related drawings directed to specific embodiments of the invention. Alternate embodiments may be devised without departing from the spirit or the scope of the invention. Additionally, well-known elements of exemplary embodiments of the invention will not be described in detail or will be omitted so as not to obscure the relevant details of the invention. Further, to facilitate an understanding of the description discussion of several terms used herein follows.

As used herein, the word "exemplary" means "serving as an example, instance or illustration." The embodiments described herein are not limiting, but rather are exemplary only. It should be understood that the described embodiments are not necessarily to be construed as preferred or advantageous over other embodiments. Moreover, the terms "embodiments of the invention", "embodiments" or "invention" do not require that all embodiments of the invention include the discussed feature, advantage or mode of operation.

"Optional" or "optionally" means that the subsequently described event or circumstance may or may not occur, and that the description includes instances in which said event or circumstance occurs and instances where it does not. For example, the phrase "optionally comprising X" means that the composition may or may not contain X, and that this description includes compositions that contain and do not contain X.

The term "consisting essentially of" excludes additional method (or process) steps or composition components that substantially interfere with the intended activity of the method (or process) or composition, and can be readily determined by those skilled in the art (for example, from a consideration of this specification or practice of the invention disclosed herein).

The invention illustratively disclosed herein suitably may be practiced in the absence of any element (e.g., method (or process) steps or composition components) which is not specifically disclosed herein.

According to at least one exemplary embodiment, a haploid *Lolium* plant may be produced by first generating a hybrid between an inducer line (IL) and either of a *L. multiflorum* or a *L. perenne*. The resulting F1 hybrid may then be selfed, and the resulting seed planted to create F2 plants, at least some of which may be haploid Loliums.

The IL used may be any suitable inducer line, such as an inducer line that has the ability to induce mitotic genome instability and haploid sectoring when hybridized with the *Lolium* paternal parent, for example the IL1 or IL2 lines as described in Kindiger and Singh, 2011; Kindiger, 2012; U.S. Pat. No. 8,618,353; and accessible via. ATCC deposit accession no. PTA-10229, and suitable progeny thereof.

Examples

Generation of Haploids

Hybrids were generated in 2015 at the Barenbrug Research Laboratory, Albany, Oreg. utilizing the IL lines as the maternal parent. The ryegrass genotypes utilized represented a small but diverse group of tetraploid *L. perenne* and *L. multiflorum* genotypes. Hybridizations were made by crossing inducer line IL1×LPT3A99 cv. (4n=4×=28); IL1× Jumbo cv. (4n=4×=28); and IL1×Remington cv. (4n=4×=28) (Table 1). LPT3A99 represents a perennial tetraploid experimental ryegrass. Jumbo represents a tetraploid, annual ryegrass. The Remington cultivar represents an intermediate, tetraploid perennial form of ryegrass. All materials were provided by Barenbrug Seeds, West Coast Research Laboratory, Albany, Oreg. USA.

Six of the generated IL×ryegrass F1 were submitted to chromosome counts and then selfed. The generated F2 seed were sent for analysis at the USDA-ARS, Grazinglands Research Laboratory, El Reno, Okla. USA. The experimental cultivar LPT3A99 provided four individuals for this study. One IL×LPT3A99 F1 possessed a tetraploid constitution (4n=4×=28). Three additional IL×LPT3A99 F1 exhibited a diploid (2n=2×=14) genome constitution. The IL×Jumbo hybridization produced one individual with a diploid (2n=2×=14) constitution. The IL×Remington produced one F1 with a diploid (2n=2×-=14) constitution.

At maturity, the F1 inflorescences were broken up by hand followed by a light cleaning to remove stems. The resulting F2 seed were then placed in trays containing a light potting soil mix for germination and seedling development. Following two to three weeks of germination, seedlings appeared and were allowed to grow to an appropriate size that allowed the phenotypic diversity to be observed. As the plants matured, the recovered seedlings were submitted to both chromosome root-tip counts (Kindiger, A technique for the preparation of Somatic Chromosomes of Maize, The Maize Handbook, 74:481-483, 1996) and flow cytometry analysis. The seedlings were eventually transferred to larger six-inch pots to allow more growth and additional phenotypic observation ( ). Over 40 F2 seed were evaluated from each F1 individual (Table 1).

TABLE 1

Offspring produced from the various IL × *Lolium* sp. Hybridizations

| F1 Hybrid | F1 Ploidy | Number and type of F2 | | | | |
| --- | --- | --- | --- | --- | --- | --- |
| | | Haploid | Diploid | Triploid | Tetraploid | Mixoploid |
| IL/LPT3A99 | 4n | 1 | 43 | 3 | 2 | 2 |
| IL/LPT3A99 | 2n | 10 | 30 | 2 | 0 | 0 |
| IL/LPT3A99 | 2n | 5 | 43 | 0 | 0 | 1 |
| IL/LPT3A99 | 2n | 8 | 35 | 8 | 0 | 0 |
| IL/Jumbo | 2n | 10 | 37 | 3 | 0 | 0 |
| IL/Remington | 2n | 14 | 33 | 3 | 0 | 0 |
| | Totals: | 48 | 269 | 19 | 2 | 3 |

Plant Material Analysis

Flow cytometry was used to analyze the ploidy of the plant hybrids produced in this study, based on published methods (Galbraith et al., Rapid flow cytometric analysis of the cell-cycle in intact plant tissues, Science 220:1049-1051, 1983; Cousin et al., An efficient high-throughput flow cytometric method for estimating DNA ploidy level in plants, Cytometry 75:1015-1019, 2009). Flow cytometry was performed on an Attune NxT flow cytometry under the following conditions and protocols.

In 2017, mature leaf samples from the greenhouse grown materials were obtained from each F1 and F2 individuals to determine if the degree of any potential genome or somatic loss could be detected. In most instances leaf samples identified obvious plant sectors through flow cytometry analysis.

For the flow cytometric analysis, approximately 0.05 g of fresh cut leaf tissue were placed in 1.5 ml Eppendorf tubes. Approximately 0.05 g of a 0.9-2.0 maceration stainless steel bead product (SSB14B, Next Advance Inc., Averill Park, N.Y., USA) and one 3.2 mm stainless steel bead (SSB32, Next Advance Inc., Averill Park, N.Y., USA) were combined for leaf maceration. 500 µL of Galbraith solution was placed in each tube (Galbraith et al., 1983) and each sample was placed in a rotary bullet blender tissue homogenizer (Next Advance Inc., Averill Park, N.Y., USA) using the manufacturer's suggested settings to macerate the leaf tissue.

Approximately 400 µL of this fluid were transferred from the Eppendorf tubes to 15 ml Corning tubes. Nuclei labelling and detection were achieved by dispensing 1 ml of the FxCycle PI/RNase staining solution (Invitrogen by Thermo Fisher Scientific, 81 Wyman Street, Waltham, Mass. 02451 USA) into the macerated leaf tissue for one hour. Following the manufacturer's staining recommendations, samples were retained in darkness during the one-hour staining interval. Prior to flow cytometric analysis each sample was filtered through a 50 µm CellTrics disposable filter (Sysmex-Partec GmbH, Goerlitz, Germany) before evaluations in a flow cytometer (Model AFC2, Thermofisher Scientific, 81 Wyman Street, Waltham, Mass. 02451 USA).

The flow cytometer was set to deliver a volume of 100 µL from the sample syringe at a flow rate of 25 µL/min. The cytometer software parameters were initiated at the "start" mode for a few seconds, prior to initiating the "record" mode. This step was performed to stabilize the sample rate and equilibrate the concentration of the dye bound to the sample nuclei. The threshold of the forward scattering (FSC) detector was placed in the "or" mode while the side scattering and fluorescence detectors were placed in the "ignore" mode. Default threshold settings were utilized for the logic control box (OR) and the forward scattering channel detector (FSC) was set at a threshold of 25.0×1000. The number of recorded events was set to 1000 with the particular event peaks being gated and average median fluorescent values were used to estimate the ploidy/genome size of the nuclei being recorded. To provide for a base line estimator for various genome size estimations, the IL1 inducer line and the Lolium cultivars LPT3A99, Jumbo, and Remington were used as controls.

Figure 1B:
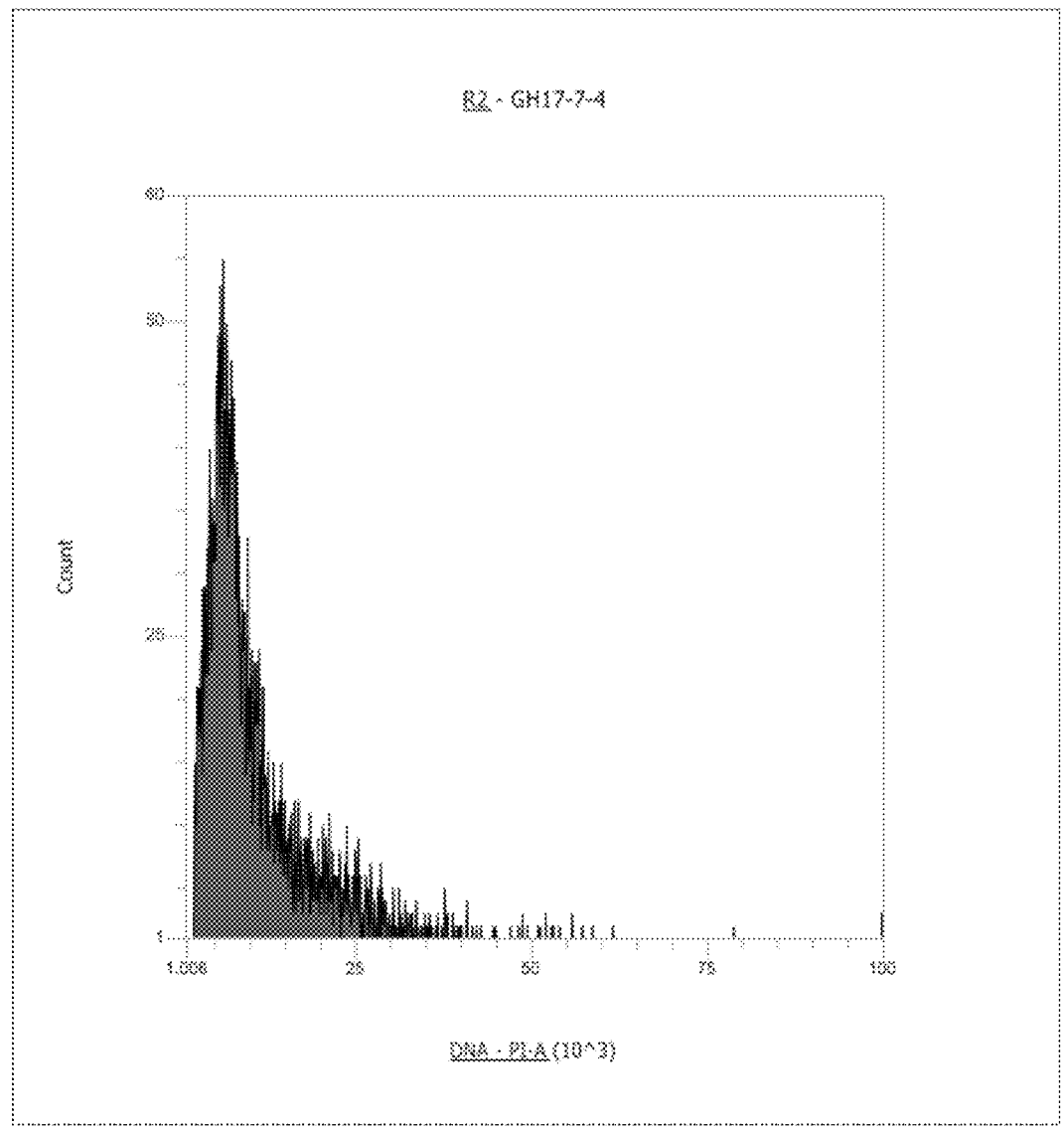
FIG. 1B shows a flow cytogram of an individual with a ryegrass phenotype exhibiting a purely haploid genome peak.

The results of the flow cytometry analysis are shown above in Table 1. Exemplary flow cytograms are shown in FIGS. 1A and 1B. In the images, the height of the peak is representative of the number of nuclei scanned possessing any particular nuclear genome size. The higher the peak, the greater the number of that particular class of nuclei. The large peaks on the left side represent haploid genome peaks. The smaller peak to the right in FIG. 1A illustrates the tetraploid F1 hybrid IL1×LPT3A99.

The genome instability and the generation of pure haploid genotypes were further confirmed by chromosome root-tip counts (data not shown).

Haploidy in recoveries utilizing the inducer lines for a *L. perenne* hybridization have been observed to range from 10% to 27.5% (Table 1). In total in the above examples, over 48 haploids were derived from 341 F2 selfs. It was observed that there was a difference in frequency of haploid generation across genotypes.

The foregoing description and accompanying FIGURES illustrate the principles, preferred embodiments and modes of operation of the invention. However, the invention should not be construed as being limited to the particular embodiments discussed above. Additional variations of the embodiments discussed above will be appreciated by those skilled in the art.

Therefore, the above-described embodiments should be regarded as illustrative rather than restrictive. Accordingly, it should be appreciated that variations to those embodiments can be made by those skilled in the art without departing from the scope of the invention as defined by the following claims.

What is claimed is:

1. A method for producing haploid *Lolium* plants, the method comprising:
   providing a *Lolium mutiflorurn* inducer line, the *L. multiflorum* inducer line having the ability to induce mitotic genome instability and haploid sectoring when hybridized as a maternal parent with a *Lolium* sp. paternal parent;
   crossing said *L. multiflorum* inducer line with a *Lolium* sp. to generate F1 plants;
   self-fertilizing at least one of the generated F1 plants;
   recovering and planting seed from the at least one self-fertilized F1 plant to generate one or more F2 plants; and
   growing said one or more F2 plants,
   wherein at least one of the one or more F2 plants is a haploid *Lolium* plant.

2. The method of claim 1, wherein the *L. multiflorum* inducer line is one of: IL1 (ATCC deposit accession no. PTA-10229), IL2 (ATCC deposit accession no. PTA-10315), and progeny thereof.

3. The method of claim 1, wherein in crossing the *L. multiflorum* inducer line with a *Lolium* sp. to generate F1 plants, the *L. multiflorum* inducer line is the maternal parent.

4. The method of claim 1, wherein the *Lolium* sp. is one of *L. multiflorum* and *L. perenne*.

5. The method of claim 1, further comprising recovering at least one of the one or more F2 plants.

\* \* \* \* \*